United States Patent
Charles et al.

(10) Patent No.: US 10,285,584 B2
(45) Date of Patent: May 14, 2019

(54) SUBTRACTIVE EN FACE OPTICAL COHERENCE TOMOGRAPHY IMAGING

(71) Applicant: NOVARTIS AG, Basel (CH)

(72) Inventors: Steven T. Charles, Germantown, TN (US); Lingfeng Yu, Rancho Santa Margarita, CA (US); Hugang Ren, Cypress, CA (US)

(73) Assignee: Novartis AG, Basel (CH)

( * ) Notice: Subject to any disclaimer, the term of this patent is extended or adjusted under 35 U.S.C. 154(b) by 88 days.

(21) Appl. No.: 15/695,608

(22) Filed: Sep. 5, 2017

(65) Prior Publication Data

US 2018/0078130 A1 Mar. 22, 2018

Related U.S. Application Data

(60) Provisional application No. 62/395,653, filed on Sep. 16, 2016.

(51) Int. Cl.
*G06K 9/00* (2006.01)
*A61B 3/10* (2006.01)
(Continued)

(52) U.S. Cl.
CPC ............ *A61B 3/102* (2013.01); *A61B 3/0025* (2013.01); *A61B 3/0041* (2013.01); *A61B 3/1225* (2013.01); *A61B 3/13* (2013.01); *G06T 5/50* (2013.01); *G06T 7/0012* (2013.01); *G06T 7/11* (2017.01); *G06T 11/00* (2013.01); *G06T 11/60* (2013.01); *G06T 2207/10101* (2013.01);
(Continued)

(58) Field of Classification Search
CPC ..... A61B 3/102; A61B 3/0025; A61B 3/0041; A61B 3/1225; A61B 3/13; A61B 3/0058; A61B 3/132; A61B 3/12; A61B 3/14; A61B 3/145; A61B 3/0066; A61B 3/005; A61B 8/10; A61B 90/37; A61B 2090/3735; A61B 2090/364; A61B 2090/371; G06T 7/11; G06T 7/0012; G06T 7/33; G06T 7/38; G06T 7/0016; G06T 7/60; G06T 5/50; G06T 11/00; G06T 11/60; G06T 2207/10101; G06T 2207/20224; G06T 2207/30024; G06T 2207/30041; G06T 2207/10016; G06T 2207/10056; G06T 2207/30101; G06T 2210/41; A61F 9/007; A61F 2009/00851; A61F 2009/00887; A61F 2009/00897; G02B 21/0012; G02B 21/22; G02B 27/0101; G02B 2027/0141
See application file for complete search history.

(56) References Cited

U.S. PATENT DOCUMENTS

| | | | |
|---|---|---|---|
| 9,560,963 B2 * | 2/2017 | Buckland | A61B 3/102 |
| 2002/0036750 A1 * | 3/2002 | Eberl | A61B 3/12 351/207 |

(Continued)

*Primary Examiner* — Jose L Couso (57) ABSTRACT

En face or 3D volumetric OCT imaging during ophthalmic surgery may be performed with an OCT scanning controller that interfaces to an OCT scanner used with a surgical microscope. The OCT scanner may generate en face images before and after surgical operations, such as retinal membrane peeling, are performed. Using digital subtraction on the en face images, an overlay image indicative of the changes from the surgical operations to the eye may be generated and overlaid onto an optical image displayed to a user of the surgical microscope.

16 Claims, 3 Drawing Sheets

(51) Int. Cl.
*G06T 7/11* (2017.01)
*A61B 3/00* (2006.01)
*A61B 3/13* (2006.01)
*G06T 7/00* (2017.01)
*G06T 11/60* (2006.01)
*A61B 3/12* (2006.01)
*G06T 5/50* (2006.01)
*G06T 11/00* (2006.01)

(52) U.S. Cl.
CPC .............. *G06T 2207/20224* (2013.01); *G06T 2207/30024* (2013.01); *G06T 2207/30041* (2013.01)

(56) References Cited

U.S. PATENT DOCUMENTS

| | | |
|---|---|---|
| 2012/0274897 A1 | 11/2012 | Narasimha-Iyer et al. |
| 2013/0158531 A1 | 6/2013 | Goldshleger et al. |
| 2015/0230702 A1* | 8/2015 | Uhlhorn ................. A61B 3/102 351/206 |
| 2016/0357003 A1* | 12/2016 | Hauger ............... G02B 21/0012 |
| 2017/0340483 A1* | 11/2017 | Rill ..................... A61F 9/00825 |
| 2018/0028056 A1* | 2/2018 | Kubota .................... G06T 7/12 |
| 2018/0256024 A1* | 9/2018 | An ........................ A61B 3/102 |

\* cited by examiner

FIG. 3

SUBTRACTIVE EN FACE OPTICAL COHERENCE TOMOGRAPHY IMAGING

BACKGROUND

Field of the Disclosure

The present disclosure relates to ophthalmic surgery, and more specifically, to subtractive en face optical coherence tomography (OCT) imaging.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

In addition to viewing the fundus, surgical microscopes may be equipped with optical coherence tomography (OCT) scanners to provide additional information about portions of eye tissue involved with the vitreoretinal surgery. The OCT scanner may enable imaging of portions of the eye that are otherwise difficult to optically distinguish using the surgical microscope.

SUMMARY

In one aspect, a disclosed method is for performing ophthalmic surgery using en face OCT imaging. The method may include viewing an interior portion of an eye of a patient using a surgical microscope and an ophthalmic lens to generate an optical image of the interior portion of the eye. Based on the optical image, the method may include sending a first command to an optical coherence tomography (OCT) scanning controller coupled to the surgical microscope for en face viewing of the interior portion of the eye, the first command instructing the OCT scanning controller to generate first scan data of the interior portion of the eye. The method may further include generating a first en face image from the first scan data, sending a second command to the OCT scanning controller instructing the OCT scanning controller to generate second scan data of the interior portion of the eye, and generating a second en face image from the second scan data. The method may still further include digitally subtracting the second en face image from the first en face image to generate a third en face image. Based on the third en face image, the method may also include generating an overlay image indicative of changes to the interior portion of the eye between the first en face image and the second en face image, and displaying the overlay image with the optical image to a user of the surgical microscope.

In any of the disclosed embodiments of the method, the changes to the interior portion of the eye may include changes resulting from surgical operations during the ophthalmic surgery performed using the surgical microscope. In the method, the surgical operations may include peeling of at least a portion of a retinal membrane, wile the overlay image may be indicative of locations of the retinal membrane.

In any of the disclosed embodiments of the method, generating the overlay image may further include detecting a tissue layer from the interior portion of the eye in the first en face image, detecting the tissue layer in the second en face image, and generating the overlay image indicative of the changes to the tissue layer.

In any of the disclosed embodiments of the method, the overlay image may indicate no changes to the tissue layer.

In any of the disclosed embodiments of the method, generating the overlay image may further include applying image processing to the second en face image to detect the changes to the interior portion of the eye.

In any of the disclosed embodiments of the method, generating the overlay image may further include identifying a mask region from the third en face image based on locations of the changes to the interior portion of the eye, and displaying an indication of the mask region in the overlay image. In the method, the mask region may be a 3D volume.

In a further aspect, an OCT scanning controller is for subtractive en face OCT imaging during ophthalmic surgery. The OCT scanning controller may include a processor having access to memory media storing instructions executable by the processor. In the OCT scanning controller, the instructions may be executable by the processor for receiving a first command for en face viewing of an interior portion of an eye of a patient undergoing ophthalmic surgery, the first command instructing the OCT scanning controller to generate first scan data of the interior portion of the eye from a surgical microscope used to perform the ophthalmic surgery. The OCT scanning controller may further include instructions for generating a first en face image from the first scan data, receiving a second command instructing the OCT scanning controller to generate second scan data of the interior portion of the eye, and generating a second en face image from the second scan data. The OCT scanning controller may still further include instructions for digitally subtracting the second en face image from the first en face image to generate a third en face image. Based on the third en face image, the instructions may include instructions for generating an overlay image indicative of changes to the interior portion of the eye between the first en face image and the second en face image, and displaying the overlay image with the optical image to a user of the surgical microscope.

In any of the disclosed embodiments of the OCT scanning controller, the changes to the interior portion of the eye may include changes resulting from surgical operations during the ophthalmic surgery performed using the surgical microscope.

In any of the disclosed embodiments of the OCT scanning controller, the surgical operations may include peeling of at least a portion of a retinal membrane, while the overlay image may be indicative of locations of the retinal membrane.

In any of the disclosed embodiments of the OCT scanning controller, generating the overlay image may further include detecting a tissue layer from the interior portion of the eye in the first en face image, detecting the tissue layer in the second en face image, and generating the overlay image indicative of the changes to the tissue layer.

In any of the disclosed embodiments of the OCT scanning controller, the overlay image may indicate no changes to the tissue layer.

In any of the disclosed embodiments of the OCT scanning controller, generating the overlay image may further include applying image processing to the second en face image to detect the changes to the interior portion of the eye.

In any of the disclosed embodiments of the OCT scanning controller, generating the overlay image may further include identifying a mask region from the third en face image based on locations of the changes to the interior portion of the eye, and displaying an indication of the mask region in the overlay image.

In any of the disclosed embodiments of the OCT scanning controller, the mask region may be a three dimensional volume.

Additional disclosed embodiments include an OCT scanner, a surgical microscope, and an image processing system.

BRIEF DESCRIPTION OF THE DRAWINGS

For a more complete understanding of the present disclosure, reference is now made to the following description, taken in conjunction with the accompanying drawings, in which.

DESCRIPTION OF PARTICULAR EMBODIMENTS

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with an ophthalmic lens for viewing through the cornea, such as a contact or non-contact lens. In order to perform any of a variety of surgical procedures, the surgeon may desire to optically scan certain portions of the fundus to generate profile depth scans of the corresponding eye tissue, such as by using an OCT scanner. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

Although OCT scanners have been integrated with the optics of surgical microscopes, OCT systems (comprising scanners and scanning controllers) typically do not directly resolve retinal membranes in contact with the retina, such as the internal limiting membrane (ILM) and the epiretinal membrane (ERM) covering the macula, which are membranes that may be only a few microns in thickness. During certain vitreoretinal surgeries, peeling of the ILM or ERM is performed by the surgeon and can be challenging due to the difficulty in optically visualizing these membranes. Even though OCT images of the retina do not directly resolve the retinal membranes, OCT images may resolve differences in retinal images with or without the retinal membrane intact (pre- and post-peeling OCT images). OCT images may further show locations of retinal membranes that are no longer attached (peeled) but where residual portions of the membranes remain, such as at the edges of a peeled region of the retina, for example.

Conventional techniques for visualizing retinal membranes during vitreoretinal surgery have included visual comparison of pre- and post-peeling OCT images, which may be difficult to interpret, time-consuming to generate and display for viewing by the surgeon, and are impractical to use during surgical procedures. Additionally, retinal membranes are often stained with a dye to improve their contrast while performing surgery using a surgical microscope. One commonly used dye is indocyanine green (ICG), which is known for retinal toxicity and is therefore not suited for repeated application. Another dye that has been reported for use in ILM staining is brilliant blue G (BBG), which is not yet approved for routine clinical use by the Food and Drug Administration (FDA). However, the general use of dyes to stain retinal membranes involves additional procedures during vitreoretinal surgery and is undesirable due to the additional steps and precautions that are indicated, particularly when using toxic dyes such as ICG.

The present disclosure relates to methods and systems for subtractive en face OCT imaging. The methods and systems for subtractive en face OCT imaging during vitreoretinal surgery disclosed herein may provide the ability to visualize locations of pre- and post-peeled retinal membranes, such as ILM and ERM, during vitreoretinal surgery. The methods and systems for subtractive en face OCT imaging during vitreoretinal surgery disclosed herein may enable the surgeon to view OCT images that show locations or regions where the retinal membranes have been peeled.

As will be described in further detail, en face, volumetric (3D) OCT imaging during vitreoretinal surgery is performed using an OCT scanning controller that is integrated with the OCT scanner and the surgical microscope. The OCT scanning controller may send commands to control operation of the OCT scanner, including for en face OCT viewing of the interior portion of the eye of a patient. In particular, en face 3D OCT imaging of retinal membrane locations may be performed pre-peeling and post-peeling (or intraoperatively after partial peeling) to generate corresponding pre- and post-peeling OCT images. The pre- and post-peeling OCT images from the same portion of the eye may be digitally subtracted in order to detect and display residual unpeeled retinal membranes, such as ILM or ERM. Alternatively, certain image processing techniques may be performed on post-peeling or partial-peeling OCT images to detect edges created as a result of peeling. After detection of peeled membrane edges in this manner, the peeled membrane edges (or edges of other specific tissue layers) may be digitally identified in the image and represented using a visual indicator, such as a digital overlay of a line or a border, which may be displayed in real time to the surgeon during vitreoretinal surgery.

Figure 1:
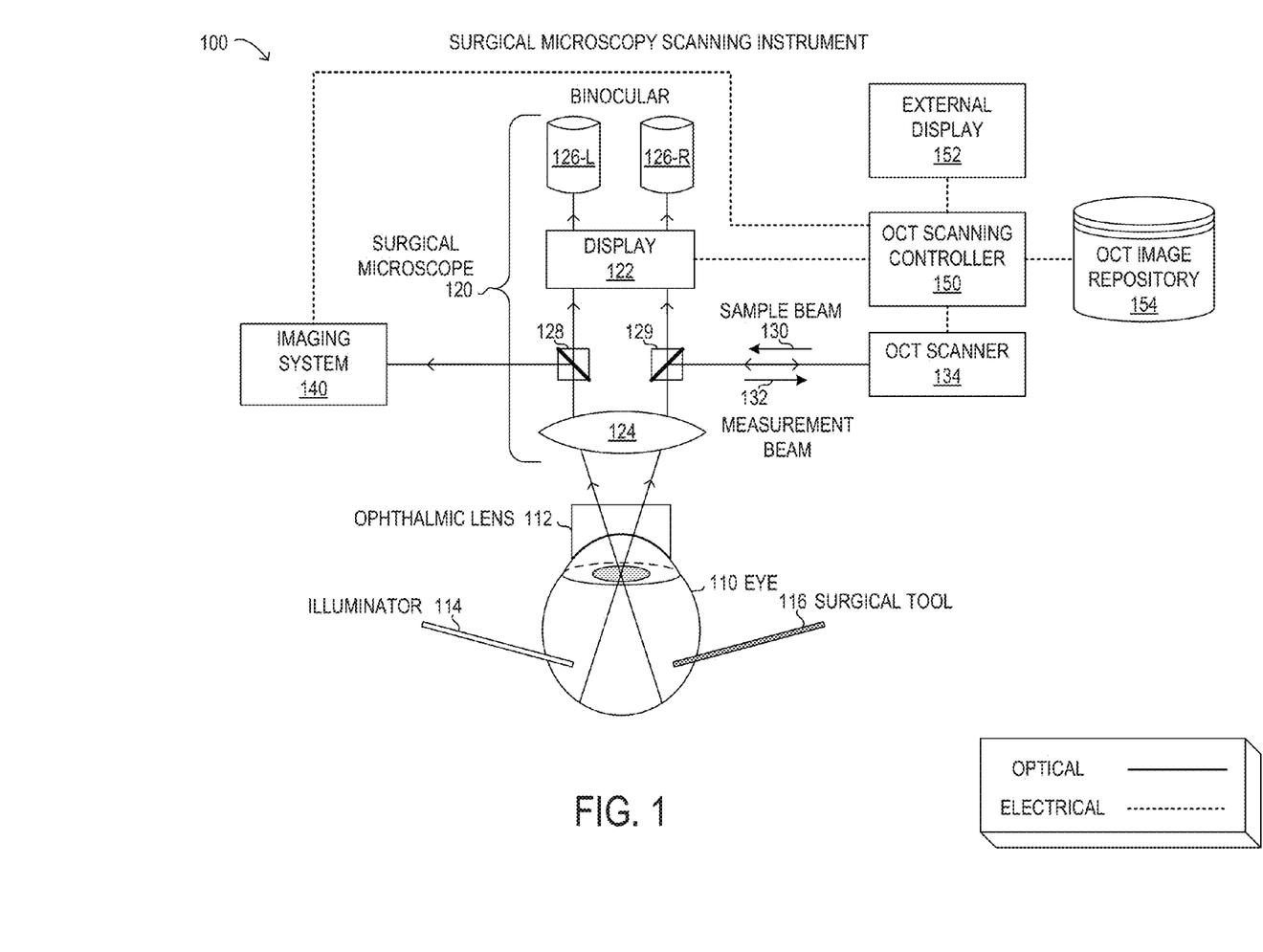
FIG. 1 is a block diagram of selected elements of an embodiment of a surgical microscopy scanning instrument.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110. As shown, instrument 100 includes surgical microscope 120, OCT scanning controller 150, external display 152, OCT image repository 154, and OCT scanner 134. Also shown in FIG. 1 are imaging system 140, ophthalmic lens 112, as well as surgical tool 116 and illuminator 114. It is noted that microscopy scanning instrument 100 may be implemented with different elements in various embodiments.

As shown in FIG. 1, surgical microscope 120 is depicted in schematic form to illustrate optical functionality. It will be understood that surgical microscope 120 may include various other electronic and mechanical components, in different embodiments. Accordingly, objective 124 may represent a selectable objective to provide a desired magnification or field of view of the fundus of eye 110. Objective 124 may receive light from the fundus of eye 110 via ophthalmic lens 112 that rests on a cornea of eye 110. Although ophthalmic lens 120 is shown as a contact lens for descriptive purposes, it is noted that various types of ophthalmic lenses 112 may be used with surgical microscope 120, including contact lenses and non-contact lenses. To perform vitreoretinal surgery, various tools and instruments may be used, including tools that penetrate the sclera, represented by surgical tool 116. Illuminator 114 may be a special tool that provides a light source from within the fundus of eye 110, among other light sources that may be used.

In FIG. 1, surgical microscope 120 is shown with a binocular arrangement with two distinct but substantially equal light paths that enable viewing with binoculars 126 that comprise a left ocular 126-L and a right ocular 126-R. From objective 124, a left light beam may be split at beam splitter 128, from where imaging system 140 and left ocular 126-L receive the optical image. Also from objective 124, a right light beam may be split at partial mirror 129, which also receives sample beam 130 from OCT scanner 134, and outputs measurement beam 132 to OCT scanner 134. Partial mirror 129 also directs a portion of the right light beam to right ocular 126-R. Display 122 may include an optoelectronic component, such as an image processing system that receives the data from OCT scanning controller 150 and generates image output data for left ocular 126-L and right ocular 126-R, respectively. In some embodiments, display 122 includes miniature display devices that output images to binoculars 126 for viewing by the user. It is noted that the optical arrangement depicted in FIG. 1 is exemplary and may be implemented differently in other embodiments.

In FIG. 1, OCT scanning controller 150 may have an electrical interface with display 122, for example, for outputting display data. In this manner, OCT scanning controller 150 may output a display image to display 122 that is viewed at binoculars 126. Because the electrical interface between imaging system 140 and OCT scanning controller 150 may support digital image data, OCT scanning controller 150 (or imaging system 140) may perform image processing in real-time with relatively high frame refresh rates, such that a user of surgical microscope 120 may experience substantially instantaneous feedback to user input for controlling the selected portion of eye 110 for scanning, as well as other operations. External display 152 may output similar images as display 122, but may represent a stand-alone monitor for viewing by various personnel during vitreoretinal surgery. Display 122 or external display 152 may be implemented as a liquid crystal display screen, a computer monitor, a television or the like. Display 122 or external display 152 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 120 in FIG. 1, imaging system 140 may receive a portion of the left light beam that enables imaging system 140 to independently process, display, store, and otherwise manipulate light beams and image data. Accordingly, imaging system 140 may represent any of a variety of different kinds of imaging systems, as desired.

As shown, OCT scanner 134 may represent an embodiment of various kinds of OCT scanners. It is noted that other types of optical scanners other than OCT scanners may be used with the arrangement depicted in FIG. 1. OCT scanner 134 may control output of sample beam 130 and may receive measurement beam 132 that is reflected back in response to photons of sample beam 130 interacting with tissue in eye 110. OCT scanner 134 may also be enabled to move sample beam 130 to the selected location indicated by the user. OCT scanning controller 150 may interface with OCT scanner 134, for example, to send commands to OCT scanner 134 indicating the selected location to generate scan data, and to receive the scan data acquired by OCT scanner 134. It is noted that OCT scanner 134 may represent various types of OCT instruments and configurations, as desired, such as but not limited to time domain OCT (TD-OCT) and frequency domain OCT (FD-OCT). In some embodiments (not shown), OCT scanner 134 may support binocular OCT in which different OCT images are generated from the left beam path and the right beam path independently from one another. In particular, the scan data generated by OCT scanner 134 may include two-dimensional (2D) scan data of a line scan and three-dimensional (3D) scan data for an area scan, which can be used to generate an en face view of the scan data. The scan data may represent a depth profile of the scanned tissue that enables imaging below a visible surface within the fundus of eye 110.

As shown, OCT image repository 154 represents a digital storage medium, such as a database or a file system and corresponding storage devices, that provides access to OCT images. Specifically, OCT images of eye 110 may be recorded in advance of retinal membrane peeling during the vitreoretinal surgery, as well as after peeling at least a portion of the retinal membrane. In this manner, the pre- and post-peeling OCT images may be stored in OCT image repository 154, such that OCT scanning controller 150 or imaging system 140 can access the pre- and post-peeling OCT images.

In operation of instrument 100, the user may view the fundus of eye 110 using binoculars 126 while vitreoretinal surgery is performed on eye 110. The user may provide user input to OCT scanning controller to initiate an OCT scan. OCT scanning controller may, in turn, communicate with OCT scanner 134 to control scanning operations and perform a real-time OCT scan to generate first scan data. The first scan data may be pre-peeling. Then, in a similar manner, after at least a portion of a retinal membrane has been peeled by the surgeon, second scan data (post-peeling) may be acquired from the same location as the first scan data. Then, OCT scanning controller 150 or imaging system 140 may generate a first en face image from the first scan data and a second en face image from the second scan data. The first en face image and the second en face image may then be processed by various methods to show an indication of the peeled retinal membrane. For example, the processing may include digital subtraction of the second en face image from the first en face image to generate a third en face image that reveals locations where the retinal membrane was peeled. It is noted that en face image registration may be performed using the first en face image prior to proceeding with the surgery. The image registration, which may be based on features in the retinal pigment epithelium (RPE), may then be used to align and orient subsequent en face images, such as the second en face image described herein.

The processing may be performed in real-time. For example, based on first scan data (pre-peeling), the second scan data (post-peeling) may be acquired as frames of a video signal, with frame rates of multiple frames per second or higher, to generate corresponding frames of third scan data as a video signal that is processes in real time, such as by OCT scanning controller 150 or imaging system 140. For example, the third scan data may result in a version of the third en face image that is a digital subtraction of the second en face image from the first en face image.

It is further noted that other structures besides the retinal membranes may be identified using digital subtraction methods between the first scan data (pre-peeling) and the second scan data (post-peeling). For example, a specific tissue layer may be digitally extracted from the first en face image, such as a nerve fiber layer, among others. Then, the same tissue layer may be extracted from the second en face image to calculate a digital subtraction solely for that tissue layer. In this manner, for example, the surgeon may receive direct feedback about any changes to other tissue layers that have occurred during surgery, including confirmation that no changes to a particular tissue layer have occurred. Furthermore, instead of a particular tissue layer in the first en face image, a specific feature within one or more tissue layers may be isolated from the first en face image for digital subtraction with the second en face image. The specific feature that then results in the third en face image may be a certain tissue structure or pathology within one or more predefined or preselected tissue layers.

In yet other embodiments, an OCT signal projection from the first scan data and the second scan data may be used to generate the first en face image and the second en face image. The OCT signal projection may be obtained using an operator on the corresponding scan data, such as a mean, maximum, minimum, sum, median, difference, or other operator.

Additionally or alternatively to the digital subtraction methods described above, the second scan data (post-peeling) or the second en face image may be processed independently of the first scan data (pre-peeling) or the first en face image to apply certain image processing methods for detecting edges created by partial retinal membrane peeling. The image processing applied to the second scan data or the second en face image may include Sobel operators, edge detection, differentiation, among other operators and digital methods that can detect membrane edges or other desired tissue features.

Whether using digital subtraction methods or image processing or various combinations thereof, once the edges of the retinal membrane (or other desired tissue feature) have been digitally detected, an overlay image based on the third en face image may be generated that displays the membrane edges (or other desired tissue feature) to a user of the surgical microscope. The overlay image may include a mask region, such as a binary mask representing the peeled (or unpeeled) regions of the retina, or other differences in tissue layers of the eye. In the overlay image, the mask region may be a 3D volume to show a particular tissue layer, such as the retinal membrane or another tissue layer. The overlay image may use various representations to show the membrane edges (or other tissue features) to the user, including, but not limited to, dots, lines, dashes, colored regions, or various combinations thereof. The overlay image may be overlaid on a current view of the surgical procedure (an optical image) that is observed using display 122, and optionally external display 152. In some embodiments, the overlay image may be integrated with the second en face image for real time display during surgery. In this manner, a practical and useful aid in identifying and locating peeled and unpeeled retinal membrane portions may be provided to the surgeon while performing vitreoretinal surgery, without having to rely on the use of potentially toxic dyes to stain membranes in the eye of the patient.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components in some embodiments.

Figure 2:
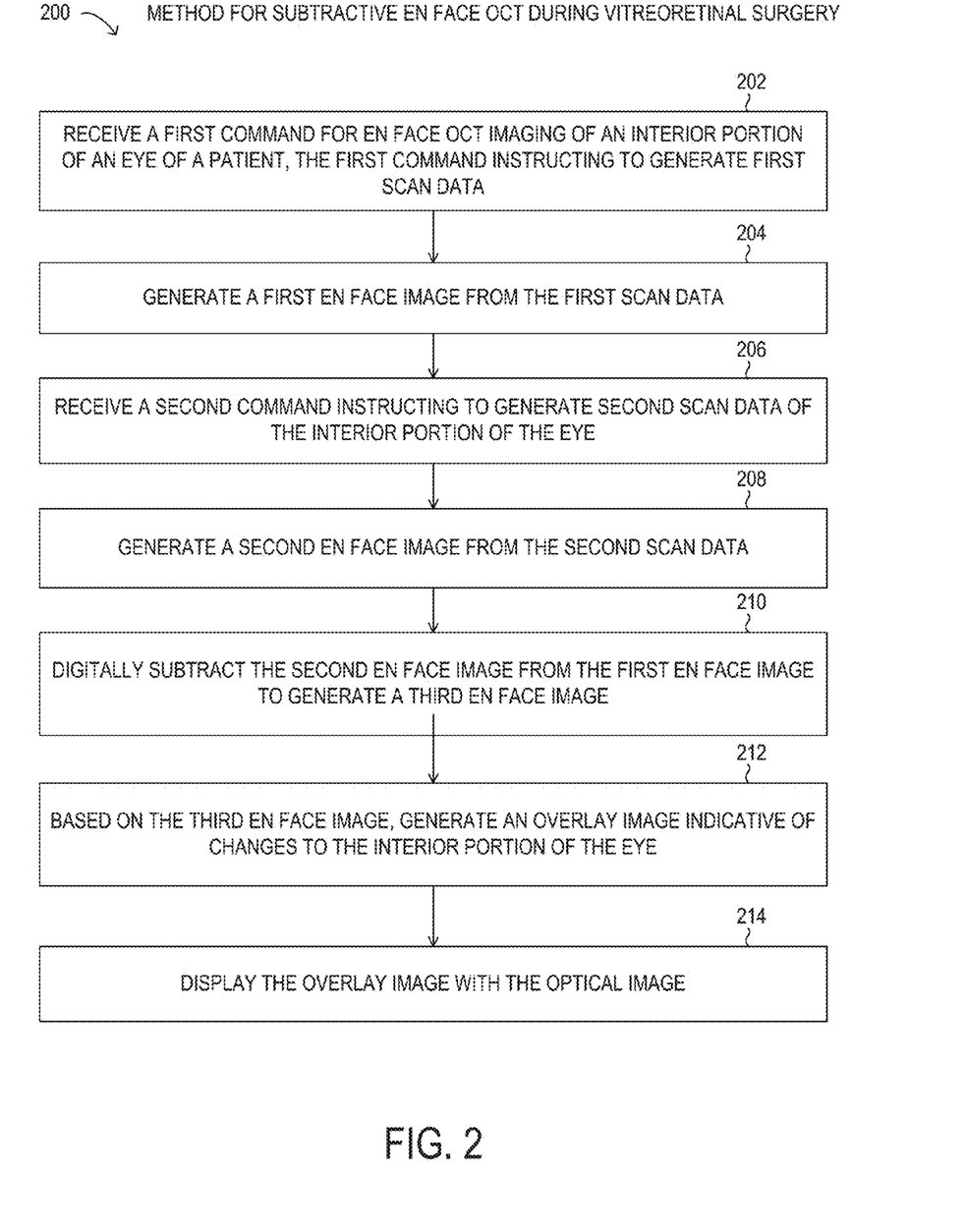
FIG. 2 is a flow chart of selected elements of a method for subtractive en face OCT during vitreoretinal surgery.

Referring now to FIG. 2, a flow chart of selected elements of an embodiment of a method 200 for subtractive en face OCT imaging during vitreoretinal surgery, as described herein, is depicted in flowchart form. Method 200 describes steps and procedures that OCT scanning controller 150 may perform while a user operates surgical microscopy scanning instrument 100 to view the fundus of an eye and perform surgical procedures based on the view of the fundus. For example, method 200 may be executed by subtractive OCT control 314 (see FIG. 3). In particular embodiments, imaging system 140 may perform at least some operations described below in method 200. It is noted that certain operations described in method 200 may be optional or may be rearranged in different embodiments.

Method 200 may begin, at step 202, by receiving a first command for en face OCT imaging of an interior portion of an eye of a patient, the first command instructing to generate first scan data. At step 204, a first en face image is generated from the first scan data. At step 206, a second command is received instructing to generate second scan data of the interior portion of the eye. At step 208, a second en face image is generated from the second scan data. At step 210, the second en face image is digitally subtracted from the first en face image to generate a third en face image. At step 212, based on the third en face image, an overlay image is generated indicative of changes to the interior portion of the eye. The changes to the interior portion of the eye in step 212 may result from surgical operations performed after the first scan data is acquired, such as peeling of a retinal membrane. At step 214, the overlay image is displayed with the optical image.

Figure 3:
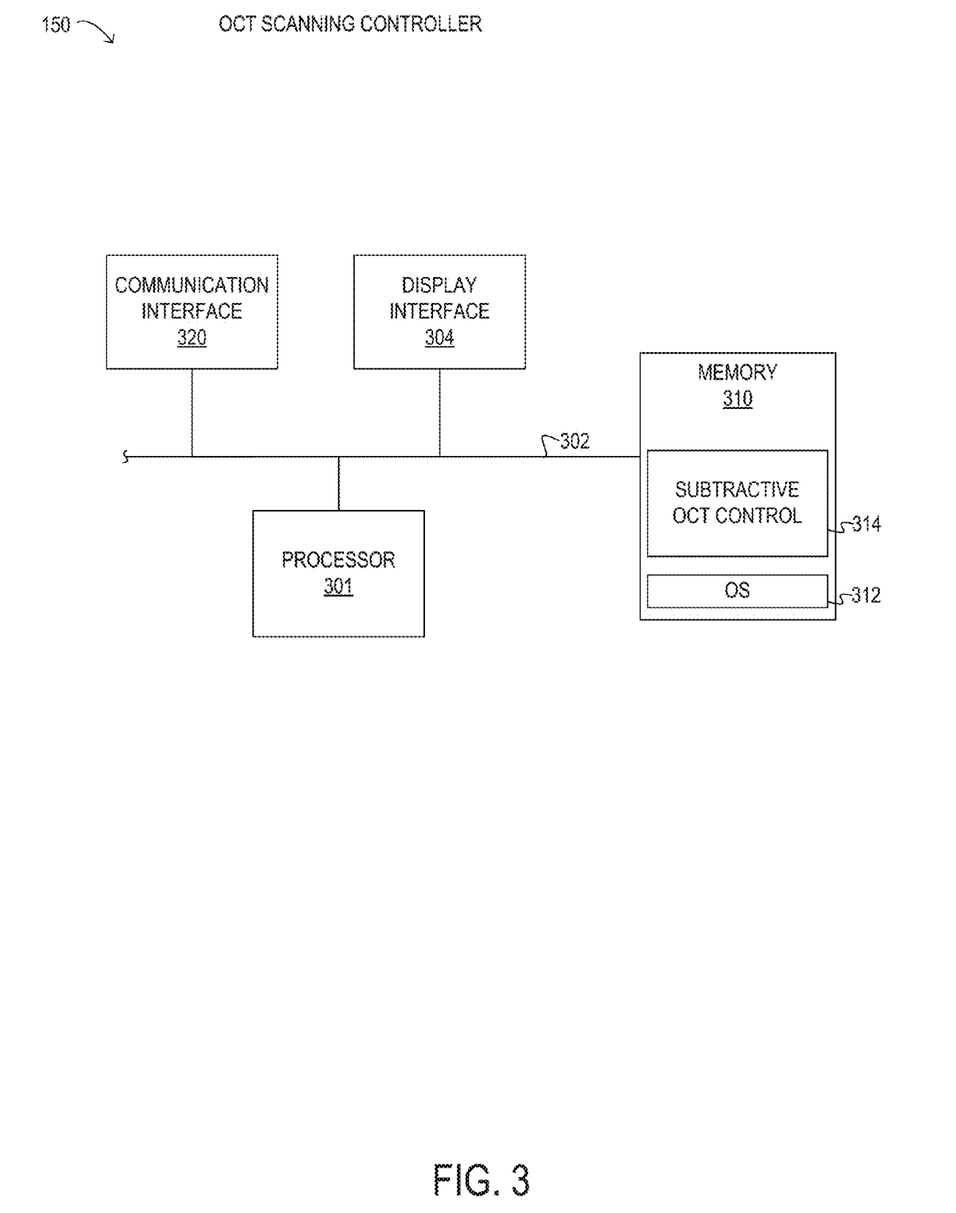
FIG. 3 is a block diagram of selected elements of an embodiment of an OCT scanning controller.

Referring now to FIG. 3, a block diagram illustrating selected elements of an embodiment of OCT scanning controller 150, described above with respect to FIGS. 1 and 2, is presented. In the embodiment depicted in FIG. 3, OCT scanning controller 150 includes processor 301 coupled via shared bus 302 to memory media collectively identified as memory 310.

OCT scanning controller 150, as depicted in FIG. 3, further includes communication interface 320 that can interface OCT scanning controller 150 to various external entities, such as OCT scanner 134, among other devices. In some embodiments, communication interface 320 is operable to enable OCT scanning controller 150 to connect to a network (not shown in FIG. 3). In embodiments suitable for subtractive en face OCT imaging during vitreoretinal surgery, OCT scanning controller 150, as depicted in FIG. 3, includes display interface 304 that connects shared bus 302, or another bus, with an output port for one or more displays, such as display 122 or an external display.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and a subtractive OCT control application 314. Operating system 312 may be a UNIX or UNIX-like operating system, a Windows® family operating system, or another suitable operating system.

As disclosed herein, en face or 3D volumetric OCT imaging during ophthalmic surgery may be performed with an OCT scanning controller that interfaces to an OCT scanner used with a surgical microscope. The OCT scanner may generate en face images before and after surgical operations, such as retinal membrane peeling, are performed. Using digital subtraction on the en face images, an overlay image indicative of the changes from the surgical operations to the eye may be generated and overlaid onto an optical image displayed to a user of the surgical microscope.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, the method comprising:
   viewing an interior portion of an eye of a patient using a surgical microscope and an ophthalmic lens to generate an optical image of the interior portion of the eye;
   based on the optical image, sending a first command to an optical coherence tomography (OCT) scanning controller coupled to the surgical microscope for en face viewing of the interior portion of the eye, the first command instructing the OCT scanning controller to generate first scan data of the interior portion of the eye;
   generating a first en face image from the first scan data;
   sending a second command to the OCT scanning controller instructing the OCT scanning controller to generate second scan data of the interior portion of the eye;
   generating a second en face image from the second scan data;
   digitally subtracting the second en face image from the first en face image to generate a third en face image;
   based on the third en face image, generating an overlay image indicative of changes to the interior portion of the eye between the first en face image and the second en face image; and
   displaying the overlay image with the optical image to a user of the surgical microscope.

2. The method of claim 1, wherein the changes to the interior portion of the eye include changes resulting from surgical operations during the ophthalmic surgery performed using the surgical microscope.

3. The method of claim 2, wherein the surgical operations include peeling of at least a portion of a retinal membrane, and wherein the overlay image is indicative of locations of the retinal membrane.

4. The method of claim 2, wherein generating the overlay image further comprises:
   detecting a tissue layer from the interior portion of the eye in the first en face image;
   detecting the tissue layer in the second en face image; and
   generating the overlay image indicative of the changes to the tissue layer.

5. The method of claim 4, wherein the overlay image indicates no changes to the tissue layer.

6. The method of claim 1, wherein generating the overlay image further comprises:
   applying image processing to the second en face image to detect the changes to the interior portion of the eye.

7. The method of claim 1, wherein generating the overlay image further comprises:
   identifying a mask region from the third en face image based on locations of the changes to the interior portion of the eye; and
   displaying an indication of the mask region in the overlay image.

8. The method of claim 7, wherein the mask region is a three dimensional volume.

9. An optical coherence tomography (OCT) scanning controller for en face OCT imaging during ophthalmic surgery, the OCT scanning controller further comprising:
   a processor having access to memory media storing instructions executable by the processor for,
      receiving a first command for en face viewing of an interior portion of an eye of a patient undergoing ophthalmic surgery, the first command instructing the OCT scanning controller to generate first scan data of the interior portion of the eye from a surgical microscope used to perform the ophthalmic surgery;
      generating a first en face image from the first scan data;
      receiving a second command instructing the OCT scanning controller to generate second scan data of the interior portion of the eye;
      generating a second en face image from the second scan data;
      digitally subtracting the second en face image from the first en face image to generate a third en face image;
      based on the third en face image, generating an overlay image indicative of changes to the interior portion of the eye between the first en face image and the second en face image; and displaying the overlay image with the optical image to a user of the surgical microscope.

10. The OCT scanning controller of claim 9, wherein the changes to the interior portion of the eye include changes resulting from surgical operations during the ophthalmic surgery performed using the surgical microscope.

11. The OCT scanning controller of claim 10, wherein the surgical operations include peeling of at least a portion of a retinal membrane, and wherein the overlay image is indicative of locations of the retinal membrane.

12. The OCT scanning controller of claim 10, wherein generating the overlay image further comprises:
    detecting a tissue layer from the interior portion of the eye in the first en face image;
    detecting the tissue layer in the second en face image; and
    generating the overlay image indicative of the changes to the tissue layer.

13. The OCT scanning controller of claim 12, wherein the overlay image indicates no changes to the tissue layer.

14. The OCT scanning controller of claim 9, wherein generating the overlay image further comprises:
    applying image processing to the second en face image to detect the changes to the interior portion of the eye.

15. The OCT scanning controller of claim 9, wherein generating the overlay image further comprises:
    identifying a mask region from the third en face image based on locations of the changes to the interior portion of the eye; and
    displaying an indication of the mask region in the overlay image.

16. The OCT scanning controller of claim 15, wherein the mask region is a three dimensional volume.

* * * * *